United States Patent
Rzhanov et al.

(10) Patent No.: US 8,568,142 B2
(45) Date of Patent: Oct. 29, 2013

(54) ROTATABLE ENDODONTIC INSTRUMENTS AND METHODS FOR THEIR MANUFACTURE

(76) Inventors: Evgueniy A. Rzhanov, Westford, MA (US); Anatoliy E. Rzhanov, Westford, MA (US)

( * ) Notice: Subject to any disclaimer, the term of this patent is extended or adjusted under 35 U.S.C. 154(b) by 417 days.

(21) Appl. No.: 12/848,135

(22) Filed: Jul. 31, 2010

(65) Prior Publication Data

US 2011/0033821 A1    Feb. 10, 2011

Related U.S. Application Data

(60) Provisional application No. 61/231,474, filed on Aug. 5, 2009.

(51) Int. Cl.
*A61C 5/02* (2006.01)

(52) U.S. Cl.
USPC .......................................................... 433/102

(58) Field of Classification Search
USPC ............................................... 433/102, 224
See application file for complete search history.

(56) References Cited

U.S. PATENT DOCUMENTS

| | | | | |
|---|---|---|---|---|
| 3,330,040 A * | 7/1967 | Kahn | ............................. | 433/224 |
| 3,906,636 A * | 9/1975 | Rainey et al. | ................. | 433/102 |
| 5,695,513 A * | 12/1997 | Johnson et al. | ............... | 606/180 |
| 6,267,592 B1 * | 7/2001 | Mays | ............................. | 433/102 |
| 6,443,730 B2 * | 9/2002 | Davidson | ....................... | 433/102 |
| 6,579,092 B1 * | 6/2003 | Senia et al. | .................... | 433/102 |
| 6,589,052 B1 * | 7/2003 | Wilcko | ......................... | 433/102 |
| 7,481,652 B2 * | 1/2009 | Senia et al. | .................... | 433/102 |
| 8,109,763 B2 * | 2/2012 | Levy et al. | ..................... | 433/102 |
| 2005/0186534 A1 * | 8/2005 | Roane | ........................... | 433/102 |

* cited by examiner

*Primary Examiner* — Ralph Lewis
(74) *Attorney, Agent, or Firm* — Roy J. Rosser

(57) ABSTRACT

A quasi-hyperbolic endodontic instrument having a cylindrical, elongated shaft with a radius that varies as a smooth, continuous curve along the length of the shaft and is larger near the distal portion of the file than near the proximal end of the file. The distal radius may be 10% or more larger than the proximal radius. This design provides a flexible file that minimizes the possibility of breaking, and ensures that if breakage does occur, it will occur near the handle, allowing the broken bit to be easily removed from the tooth canal. The instrument may further, or instead, have a metal cable connecting the cutting head to the handle to help reduce metal fatigue.

3 Claims, 6 Drawing Sheets

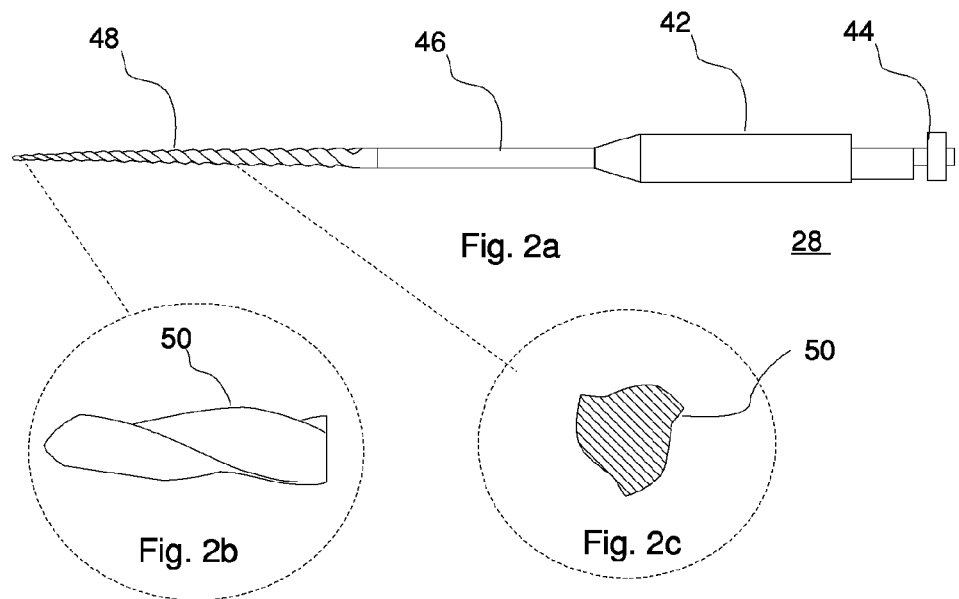
PRIOR ART
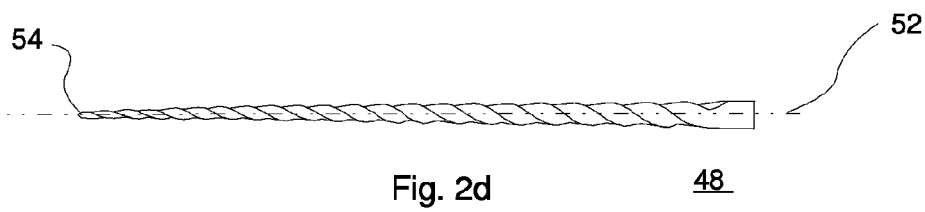
PRIOR ART

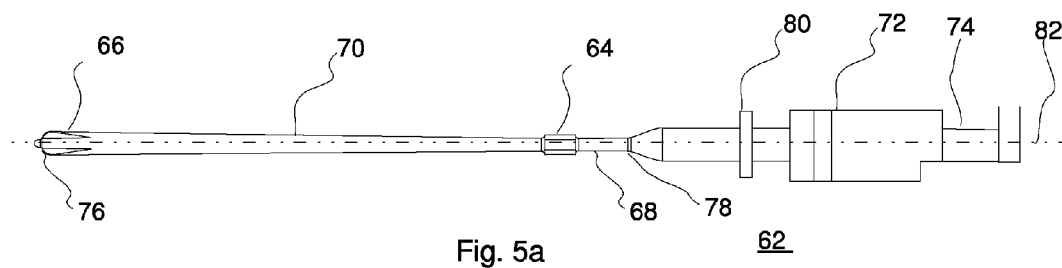
Fig. 5a
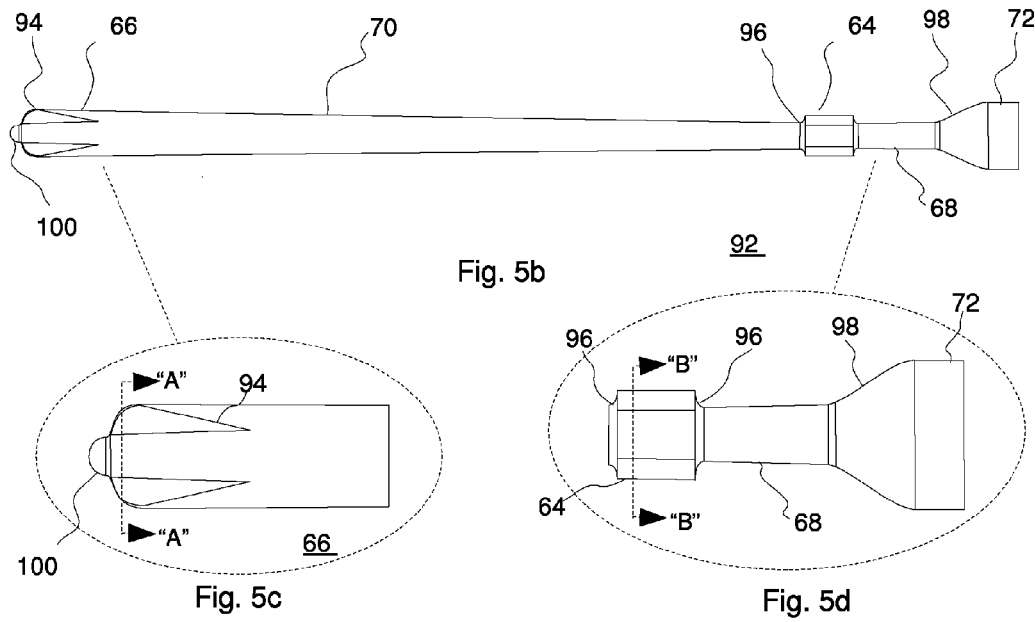
Fig. 5b
Fig. 5c
Fig. 5d
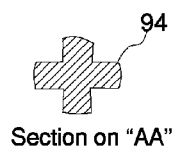
Section on "AA"
Fig. 5e
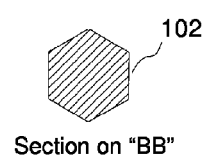
Section on "BB"
Fig. 5f

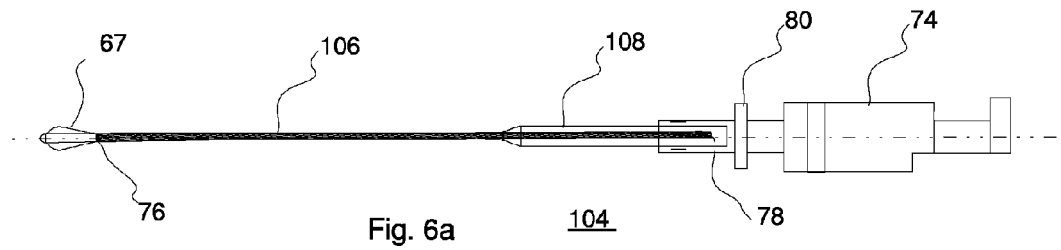
Fig. 6a
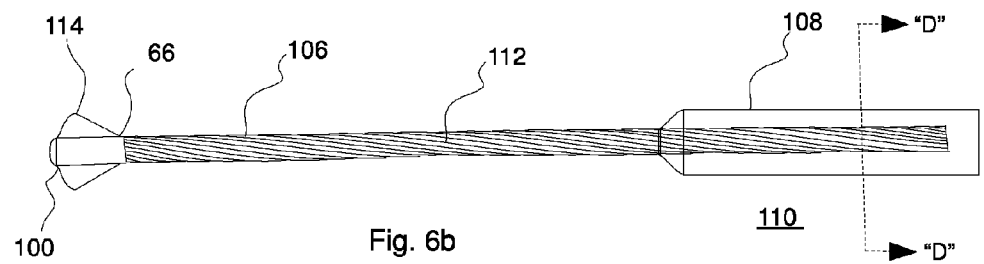
Fig. 6b
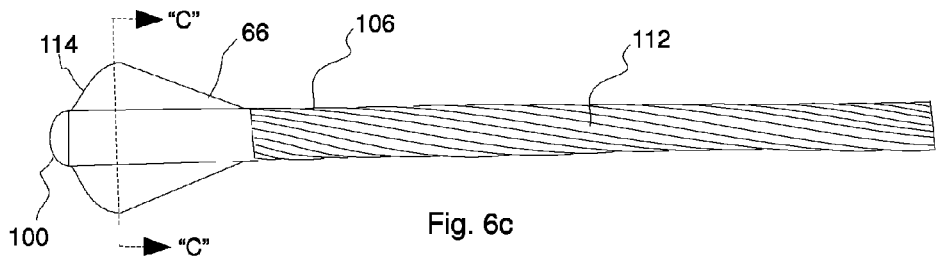
Fig. 6c
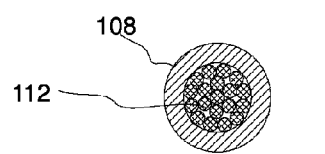
Cross-section on "DD"
Fig. 6e
Cross-section on "CC"
Fig. 6d
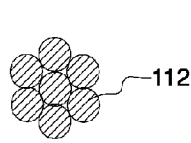
Fig. 6f
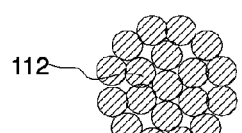
Fig. 6g

ROTATABLE ENDODONTIC INSTRUMENTS AND METHODS FOR THEIR MANUFACTURE

CROSS REFERENCE TO APPLICATIONS

This application is related to, and claims priority from, U.S. Provisional Patent Application No. 61/231,474 filed on Aug. 5, 2009 by E. Rzhanov et al. titled "High Safety Files for Root Canal Treatment", the contents of which are hereby incorporated by reference.

TECHNICAL FIELD

The present invention relates to endodontic instruments and their method of manufacture, and more particularly, to rotatable endodontic instruments having radius profiles and structures that produce a favorable distribution of torsion angle per unit length along the length of the instrument and/or reduce metal fatigue associated with repeated use of the instrument.

BACKGROUND ART

Endodontic therapy is a dental procedure, colloquially know as a "root canal", undertaken to repair and save a tooth by removing and replacing infected dental pulp.

FIG. 1a show a cross-section of an exemplary healthy tooth 10. The main body 12 of the tooth is composed of dentin, a matrix of mineralized connective tissue, that supports an overlay of hard, brittle tooth enamel 14. The main body 12 of the tooth is supported by the gums 16 that cover the jaw bone 18, and also contains dental pulp 20, a soft connective tissue. Nerves in the dental pulp 20 connect with the rest of the body via one or more canals 22 located in the roots of the tooth 24.

When dental pulp 20 becomes irritated, it swells up. Since the dental pulp 20 is encased in a rigid matrix of dentin, there is little or no room for expansion and the nerves in the dental pulp 20 are squeezed or pinched, causing a great deal of pain. A "root canal" is an endodontic procedure designed to alleviate this pain and save the tooth by removing the dental pulp 20 and replacing it with a bio-inert material such as gutta-percha.

FIG. 1b shows the first step in a typical root canal procedure. A portion of the tooth enamel 14 has been removed, along with a portion of the main body 12 of the tooth and the bulk of the dental pulp 20. This removal is typically effected using a tungsten carbide, or diamond, tipped dental bur 26, a.k.a. a dental drill bit.

FIG. 1c shows a further step in a typical root canal procedure. At this stage, the dental pulp 20 has been removed from the right hand canal 22, and the dental pulp 20 is in the process of being removed from the left hand canal 22 by means of an endodontic instrument 28.

FIG. 1d shows a completed root canal treatment. The dental pulp 20 has been completely removed and replaced by a bio-inert material 34.

FIG. 2a shows an exemplary, prior art, endodontic instrument 28 used to remove dental pulp 20 from the canals 22 in a root canal procedure. The endodontic instrument 28 has a shank 42, a quick change, cam drill holder 44, a cylindrical shaft 46 and a flexible cutting bit 48. The cam drill holder 44 may be one of the standard handles for connecting the endodontic instrument 28 to an endomotor.

Prior art endodontic instruments 28 are typically made from a Nickel-Titanium (NiTi) alloy. NiTi alloys are more flexible than more conventional stainless steels, but are subject to metal fatigue and may break after repeated use, or after a number of flexures in a single use. Prior art endodontic instruments 28 also typically have screw shaped flexible cutting bits 48 that may result in the bit becoming "screwed in" to the canals 22, creating a situation where the flexible cutting bit 48 may be torsionally overloaded. Prior art endodontic instruments 28 typically have a tapered, or conical, flexible cutting bit 48 that narrows down from the proximate end of the bit to the distal end.

FIG. 2b shows a close-up view of the distal end of a prior art endodontic instrument 28. FIG. 2b clearly showing the screw shaped cutting edge 50.

FIG. 2c shows a close-up view of a cross-section of the flexible cutting bit 48 of a prior art endodontic instrument 28 showing the cutting edges 50.

FIG. 2d shows a close up view of the flexible cutting bit 48 of a traditional rotary NiTi endodontic instrument 28. FIG. 2d clearly shows the tapered, or conical, flexible cutting bit 48 that narrows down from the proximate end of the bit to the distal end.

In use, the endodontic instrument 28 may be attached by the cam drill holder 44 to a rotary drill or rotary endomotor. The endomotor, which may be an electrically powered drill, applies a torque to the endodontic instrument 28 that is transmitted via the handle the shank 42 to the flexible cutting bit 48. The applied torque results in a slight twisting of the flexible cutting bit 48 as the cutting edges 50 engage the dental pulp 20 in the canals 22 and the surrounding dentin in the main body 12.

FIG. 3a shows a plot of c(z), the torsional rigidity of a NiTi flexible cutting bit 48, measured in dyne·cm$^2$, as a function of distance along the axis 52 of the flexible cutting bit 48, measured in cm.

The plot 56 is calculated for a NiTi flexible cutting bit 48 having a diameter $D_0$ at the distal end 54 of 0.25 mm. The distal end 54 is also where z, the distance along the axis 52, is taken to be zero. The length L of the flexible cutting bit is 16 mm and the cone shape of the flexible cutting bit 48 is 2%, i.e., the radius of cross-section increases by 0.02 mm along each mm from the tip of instrument.

From plot 56, it is evident that the torsional rigidity of the flexible cutting bit 48 is at its least at the distal end 54, where the radius of the flexible cutting bit 48 is smallest.

FIG. 3b shows $\tau(z)$, the torsion angle per unit length, of the same NiTi flexible cutting bit 48, plotted as a function of distance z, measured in cm, along the axis 52 of the flexible cutting bit 48. $\tau(z)$, the torsion angle per unit length, is shown for two different values of applied torque when the tip of the endodontic instrument 28 is held stationary.

Plot 58 shows the torsion angle per unit length $\tau(z)$ of the typical, conical endodontic instrument 28 when a torque of 100 dyne·cm is applied to the shank 42 while the distal end 54 is held stationary.

Plot 60 shows the torsion angle per unit length $\tau(z)$ of the typical, conical endodontic instrument 28 when a torque of 150 dyne·cm is applied to the shank 42 while the distal end 54 is held stationary. These plots are based on mathematical analysis shown in detail in, for instance, U.S. Provisional Patent Application No. 61/231,474 filed on Aug. 5, 2009 by E. Rzhanov et al. titled "High Safety Files for Root Canal Treatment", the contents of which are hereby incorporated by reference.

From these plots, it is evident that the torsion angle per unit length $\tau(z)$ will most probably first exceed some upper critical value in the vicinity of the distal end 54 of the endodontic instrument 28. This is where the flexible cutting bit 48 is located. The flexible cutting bit 48, particularly the distal end of the flexible cutting bit 48, is, therefore, where any excessive torque applied to the endodontic instrument 28 will most likely begin to deform the endodontic instrument 28, and it is also the region where any breakage is most likely to occur.

When a flexible cutting bit 48 breaks deep in a canal 22, it is often impossible to retrieve the broken portion. The broken, distal portion of the flexible cutting bit 48, therefore, often has to be left in place where it broke in the canal 22. This is not a very satisfactory outcome for the patient as it sometimes means that the tooth then has to be removed, which is what the root canal procedure was intended to avoid.

An endodontic instrument 28 with a cutting bit that is flexible, robust and not inclined to break is, therefore, highly desired. It is further highly desired that the endodontic instrument 28 is manufactured so that, if breakage does occur, the distal portion of the broken instrument may be easily removed from the patient's tooth.

SUMMARY OF INVENTION

Technical Problem

The technical problem addressed by the present invention includes, but is not limited to, providing a flexible cutting bit suitable for endodontic therapy, that is shaped, or constructed, so as to minimize the possibility of the bit breaking. Significant causes of bit breakage include excessive torsional force and metal fatigue from repeated flexing. Moreover, the flexible cutting bit is preferably shaped, or constructed, so that, if breakage does occur, it will most likely occur in a portion of the endodontic instrument that allows the distal portion of the broken bit to be easily removed from the tooth, even when the distal end of the tip is trapped deep in a dental pulp canal.

Solution to Problem

The present invention solves the technical problem by providing a quasi-hyperbolic endodontic instrument having a cylindrical, elongated shaft with a radius that is a smooth, continuous curve. Moreover, the radius of the elongated shaft is larger near the working, or distal, portion of the file than near the handle, or proximate end, of the instrument. The distal radius may, for instance, be 10% or more, larger than the proximal radius. This design provides a flexible instrument that reduces the possibility of the instrument breaking, and helps ensure that if breakage does occur, it will occur near the handle, allowing the broken bit to be easily removed from the tooth canal.

In a preferred version, the working portion of the instrument, i.e., the portion located near the shaft's distal end, extends less than one-third of the way along the shaft and is shaped to have at least one cutting surface. The instrument may also have a capture node, located near the handle, or proximal end, of the shaft. The capture node may have an effective radius that is 10% or more larger than the radius of the shaft at the place where the shaft joins the capture node. The endodontic instrument of this invention may also have a region of weakest torsional rigidity located between the capture node and the proximal end of the shaft, ensuring that if the file does break, the capture node will remain attached to the broken off end that is lodged in the tooth canal. The capture node may have one or more flat or grippable facets on its outer surface, so that tweezers, flat pliers, or a specially designed capture tool, may easily grip and remove the broken end from the tooth canal.

In a further embodiment of the invention, the technical problem may be solved by providing a flexible endodontic instrument having a metal cable. A cutting head may be attached to the distal end of the cable, while the proximal end of the cable may be attached to a handle.

In a further preferred embodiment of the invention, the cable may have at least seven strands of metal wire of equal lengths, with six of the strands being helically wound around the seventh strand, to form the cable.

The handle may be made of a tube surrounding, and attached to, the cable. The tube forming the handle may extend for a third or more of the length of the cable. The tube may ensure the endodontic instrument is of the required length, while the length of the free cable from the handle to the cutting blade is of sufficient length to provide the required stiffness and flexibility.

The cable connection between the handle and the blade provides flexibility. It also tends to increase the safety of the file, as the fibers in a cable tend to be tension loaded. The torsion loading on the cable is, therefore, significantly less than it would be on a solid rod made of the same material. This allows each of the cable fibers to work within the elastic range of the metal it is made from, thereby avoiding any accumulating damage and significantly reducing the probability of deformation or breakage of the instrument.

In further embodiments, the invention may combine or incorporate elements from each of the embodiments described above.

Advantageous Effects of Invention

Advantages effects of the invention include, but are not limited to, providing endodontic instruments that have the required flexibility and cutting ability but are less susceptible to breakage than existing endodontic instruments.

These and other features of the invention will be more fully understood by references to the following drawings.

BRIEF DESCRIPTION OF DRAWINGS

FIG. 2a shows a schematic side view of an exemplary, prior art, endodontic instrument.

FIG. 2b shows a schematic close-up view of the distal end of a prior art flexible cutting bit.

FIG. 2c shows a schematic close-up view of a cross-section of a prior art flexible cutting bit.

FIG. 2d shows a schematic close up view of a prior art flexible cutting bit.

FIG. 5a shows a schematic, side view of an exemplary quasi-hyperbolic endodontic instrument of the present invention.

FIG. 5b shows a schematic side view of an exemplary quasi-hyperbolic endodontic file FIG. 5c shows a schematic, close-up view of the working portion of the quasi-hyperbolic endodontic file.

FIG. 5d shows a close-up schematic view of the proximal end of the quasi-hyperbolic endodontic file.

FIG. 5e shows a cross-sectional view drawn on "AA".

FIG. 5f shows a cross-sectional view drawn on "BB".

FIG. 6a shows a schematic, sectional side view of a cable endodontic instrument of the present invention.

FIG. 6b shows a view of an exemplary cable endodontic file of the present invention.

FIG. 6c shows the cable 106 attached to the working portion 66 of the cable endodontic file.

FIG. 6d shows a cross section on "CC".

FIG. 6e shows a cross-section on "DD".

FIG. 6f shows a cross-section view of a cable have seven strands of metal wire.

FIG. 6g shows a cross-section view of a cable 106 have nineteen strands of metal wire 112.

DESCRIPTION OF EMBODIMENTS

Embodiments of the present invention will now be described in detail by reference to the accompanying drawings in which, as far as possible, like elements are designated by like numbers.

Figure 1A:
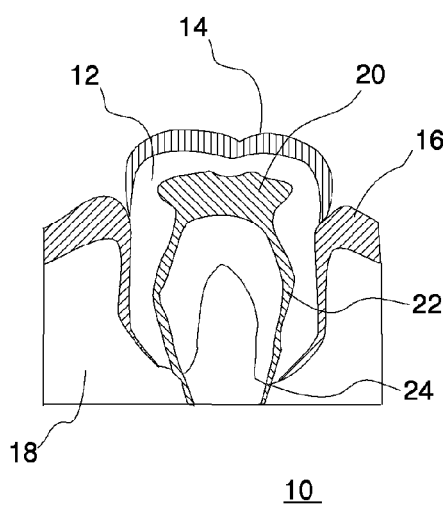
FIG. 1a shows a schematic cross-section of an exemplary healthy tooth.
Figure 1B:
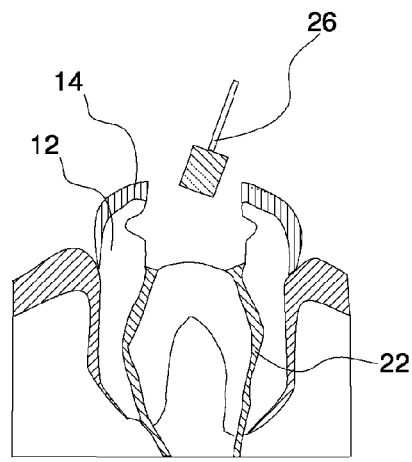
FIG. 1b shows a schematic view of a first step in a root canal procedure.
Figure 1C:
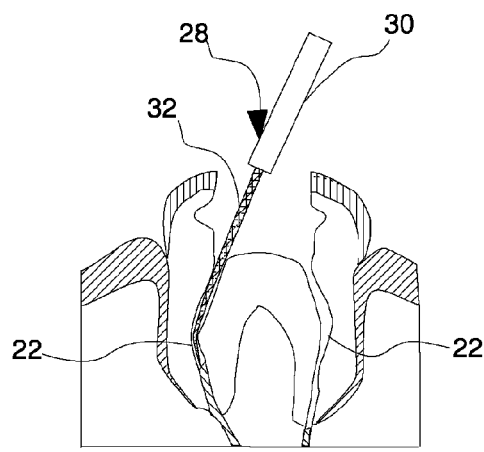
FIG. 1c shows a schematic view of an endodontic instrument being used to remove dental pulp from a tooth canal.
Figure 1D:
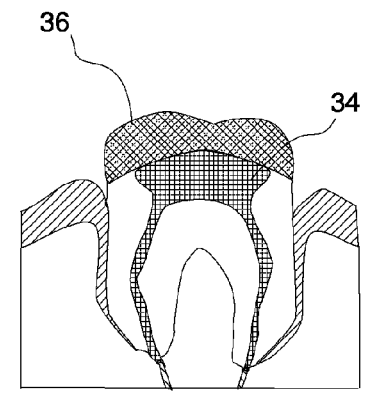
FIG. 1d shows a schematic view of a final stage of a root canal in which the dental pulp has been replaced by a bio-inert material.
Figure 3A:
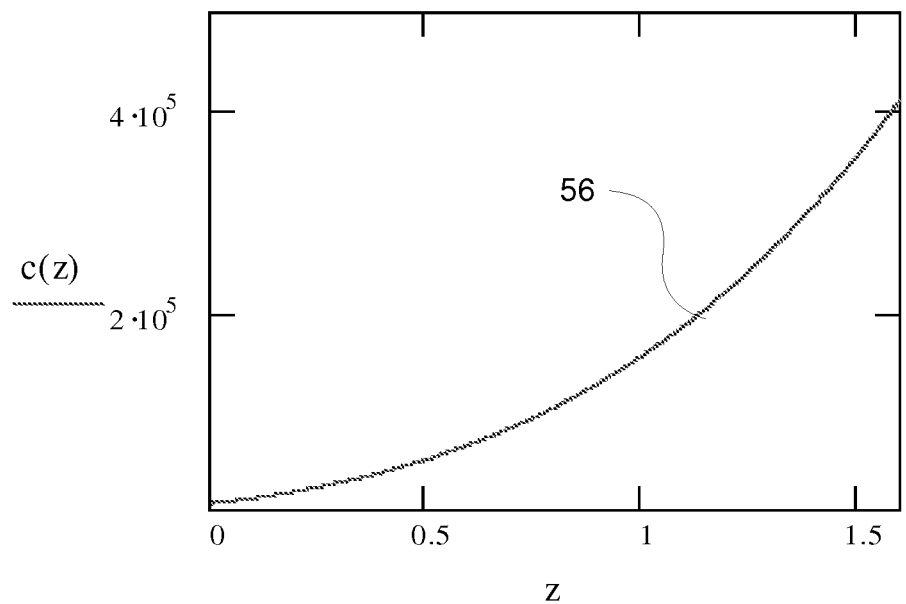
FIG. 3a shows a plot of c(z), the torsional rigidity, of a prior art NiTi flexible cutting bit as a function of distance along the axis.
Figure 3B:
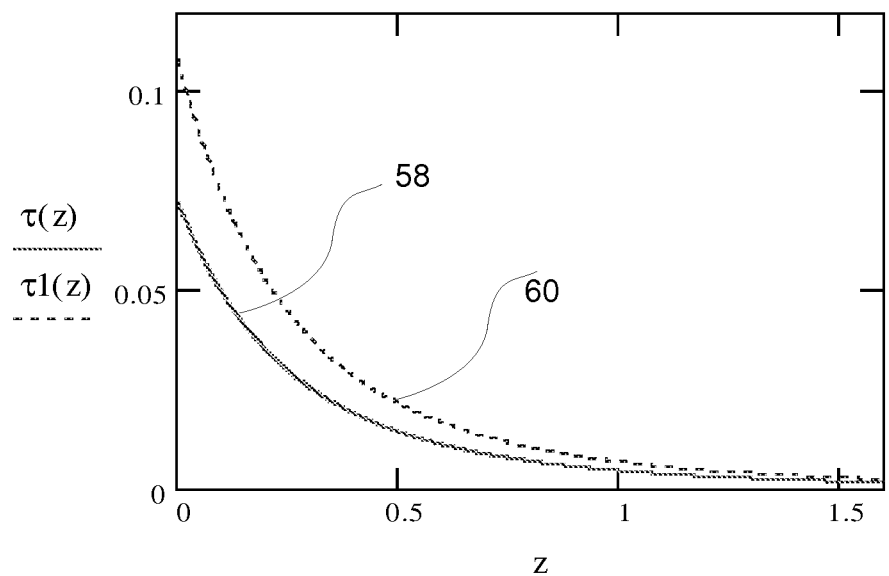
FIG. 3b shows plots of $\tau(z)$, and $\tau 1(z)$ as a function of distance (z) along the axis.
Figure 4A:
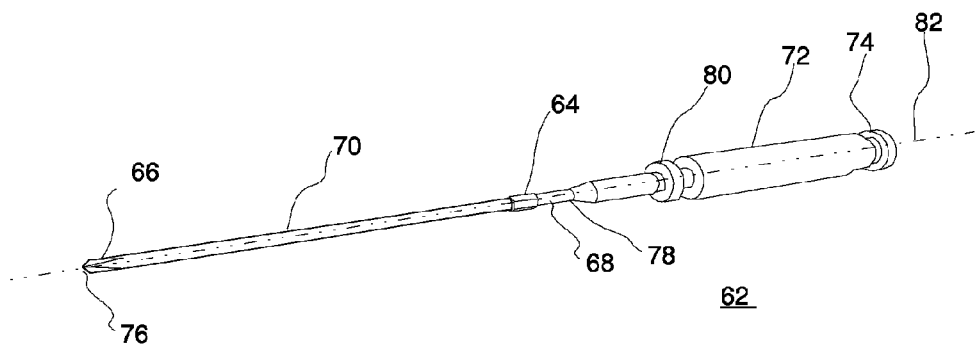
FIG. 4a shows a schematic, 3D, view of an exemplary quasi-hyperbolic endodontic instrument of the present invention.

FIG. 4a shows a schematic, 3D, view of an exemplary quasi-hyperbolic endodontic instrument 62 of the present invention. The quasi-hyperbolic endodontic instrument 62 includes a working portion 66, a flexible shaft 70, a handle 72 and a drill attachment mechanism 74. The quasi-hyperbolic endodontic instrument 62 may also include a capture node 64 and a region of weakest torsional rigidity 68. The capture node 64 may be located near the proximal end 78 of the flexible shaft 70. The working portion 66 of the reverse curved endodontic instrument 62 may be located near the distal end 76 of the flexible shaft 70. The working portion 66 may have one or more cutting edges, and typically extends for as little as 5% of the flexible shaft 70, though it may be as much as 20% or even 33% of the length of the flexible shaft 70. The flexible shaft 70 is preferably made from a suitable metal or metal alloy such as, but not limited to, a NiTi alloy, a stainless steel alloy, silver, gold, titanium or a super-elastic Nickel, Titanium and Niobium alloy or some combination thereof. The flexible shaft 70 may be rotationally symmetric about a central axis 82. The radius of the flexible shaft 70 at its distal end 76 may be about 10% or more larger than the radius of the flexible shaft 70 near its junction with the capture node 64. The capture node 64 may have one or more flat or grippable surfaces. In a preferred embodiment the cross-section of the capture node 64 may be a polygon, and preferably a regular polygon, such as, but not limited to, a triangle, a square, a pentagon, a hexagon, or an octagon. The handle 72 of the reverse curved endodontic instrument 62 may also include a depth indicator 80.

Figure 4B:
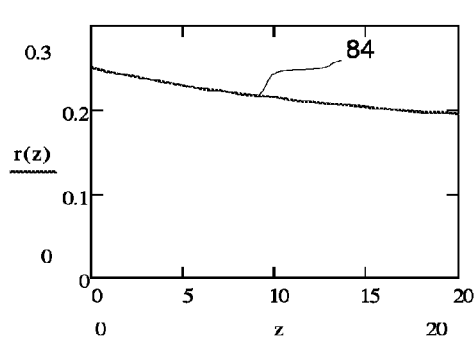
FIG. 4b show a plot of radius as a function of distance for an exemplary quasi-hyperbolic endodontic instrument.

FIG. 4b show a plot 84 of r(z), the radius r as a function of z, the position along the central axis 82 of the flexible shaft 70, of an exemplary quasi-hyperbolic endodontic instrument 62.

In a preferred embodiment, the flexible shaft 70 has a circular cross-section. The radius profile of the flexible shaft 70 is a smooth curve that is larger at the distal end (z=0) than at the proximal end (z=20). In the example shown, the distal radius is approximately 25% larger than the proximal radius. In various embodiments of the present invention, the distal radius may be only 10% larger the proximal radius, or it may be larger by a factor greater than 10% depending on factors such as, but not limited to, the material the flexible shaft 70 is made from, its length, the required flexibility or some combination thereof.

Figure 4C:
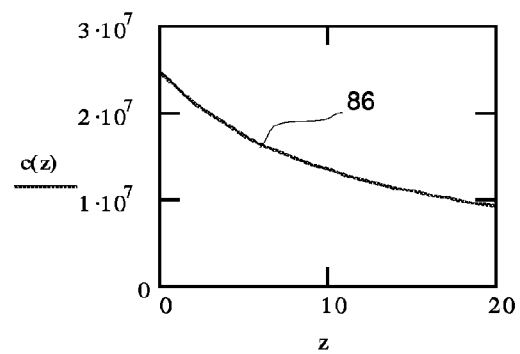
FIG. 4c shows a plot of torsional rigidity as a function of position along the central axis an NiTi flexible shaft having the radius profile shown in FIG. 4b.

FIG. 4c shows a plot 86 of c(z), the torsional rigidity as a function of position along the central axis 82 for a NiTi flexible shaft 70 having the radius profile in FIG. 4b. The torsional rigidity is greatest at the distal end of the flexible shaft 70 and a minimum at the proximal end of the flexible shaft 70.

Figure 4D:
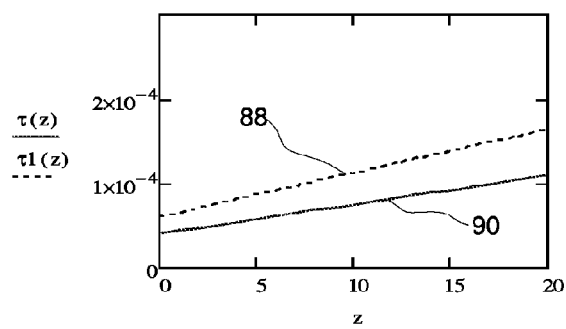
FIG. 4d show plots of τ(z), the torsion angle per unit length as a function of position along the central axis an NiTi flexible shaft having the radius profile shown in FIG. 4b.

FIG. 4d show plots of τ(z), the torsion angle per unit length as a function of z, the position along the central axis 82.

Plot 90 of τ(z) corresponds to a NiTi flexible shaft 70 having a radius profile corresponding to the hyperbolic function 91:

$$r(z) = \frac{k}{\sqrt[4]{z+a}}$$

and a torque load of 1000 dyne·mm. _k and a are engineering parameters that determine the radius of the flexible shaft 70 at the distal end 76 and the region adjacent to the capture node 64 respectively.

In plot 90, torsion angle per unit length τ increases substantially linearly with z. Torque loading on the flexible shaft 70 is, therefore, greatest near the handle and decreases toward the distal end of the flexible shaft 70. If the quasi-hyperbolic endodontic instrument 62 is subject to excess torque, breakage will, most likely, occur at the proximal end of the flexible shaft 70. As the proximal end tends to usually be clear of the tooth canal 22, there should usually be an exposed portion of the broken flexible shaft 70 that may be used to extract it from the tooth.

The hyperbolic function 91 corresponds to the optimum radius profile for the flexible shaft 70 based on equations derived in, for instance, U.S. Provisional Patent Application No. 61/231,474 filed on Aug. 5, 2009 by E. Rzhanov et al. titled "High Safety Files for Root Canal Treatment", the contents of which are hereby incorporated by reference.

Such equations include, for instance, a fundamental relation relating torsional rigidity c(z) and the torsion angle per unit length τ(z) to the applied torque M:

$$C(z) \cdot \tau(z) = M$$

Other related or similar radius profiles may be used so long as they provide a uniform distribution of torsion rigidity, having no extremes, or discontinuities, along the flexible shaft 70. Moreover, the distribution of torsion angle per unit length on the flexible shaft 70 should be a slightly increasing function of z such as, but not limited to, a linear function with a small inclination. The slight increase of torsion angle per unit length τ(z) with z compensates for practical uncertainties such as, but not limited to, inhomogeneity of the material used to manufacture the flexible shaft 70, defects introduced during manufacture, damage as a result of storage, transportation, packaging or prior use, or some combination thereof. The slight increase of torsion angle per unit length τ(z) helps ensure that any breakage is most likely to occur at the proximal end of the flexible shaft 70, close to the handle, allowing for easy retrieval of the broken bit.

In order to minimize the effect of uncertainties associated with manufacture, the flexible shaft 70 is preferably made by grinding and polishing a substrate to the correct shape and surface smoothness. Good surface smoothness helps ensure that the correct torque is applied to the working portion 66 during an endodontic procedure. The instruments should also be carefully examined using instrumentation designed for nondestructive testing and detection of flaws in metal objects such as, but not limited to, the well known supersonic reflectoscope and the well known phased-array, ultrasonic test instruments, or some combination thereof.

Plot 88 of τ(z) corresponds to a NiTi flexible shaft 70 having a radius profile corresponding to the hyperbolic function and a torque load of 1500 dyne·mm.

FIG. 5a shows a schematic, side view of an exemplary quasi-hyperbolic endodontic instrument 62 of the present invention. The quasi-hyperbolic endodontic instrument 62 includes a working portion 66, a flexible shaft 70, a handle 72 and a drill attachment mechanism 74. The quasi-hyperbolic endodontic instrument 62 may also include a capture node 64 and a region of weakest torsional rigidity 68.

FIG. 5b shows a schematic side view of an exemplary quasi-hyperbolic endodontic instrument 92.

In one embodiment of the present invention, there is a pilot tip 100. The pilot tip 100 may be shaped as a portion of a sphere, such as, but not limited to, a hemisphere. The pilot tip 100 preferably has a diameter that is about 50% of the largest diameter of the flexible shaft 70, though it may vary from 20% to 80% of that diameter. The pilot tip 100 is intended to help guide the reverse-curved endodontic instrument 62 down the canals 22 during removal of the dental pulp 20, and avoid, for instance, the instrument being misdirected down a side canal.

In one embodiment of the present invention, there is a capture node 64 that is hexagonal in cross-section. The capture node 64 may serve as a clamping point during calibration of the quasi-hyperbolic endodontic instrument 92 to determine permissible torque loads. As the region of weakest torsional rigidity 68 is located between the capture node 64 and the handle 72, if breakage does occur, the capture node 64 will most likely stay attached to the portion of the quasi-hyperbolic endodontic instrument 92 that has lodged in the tooth canal. The broken quasi-hyperbolic endodontic instrument 92 may, therefore, be easily removed using a tool such as, but not limited to, a pair of tweezers, a pair of flat nosed pliers or a specially designed tool such as, but not limited to, the special removal tool described in, for instance, U.S. Provisional Patent Application No. 61/231,474 filed on Aug. 5, 2009 by E. Rzhanov et al. titled "High Safety Files for Root Canal Treatment", the contents of which are hereby incorporated by reference, or some combination thereof.

The capture node 64 may be joined to the flexible shaft 70 by means of a smooth curve 96 that avoids any discontinuities in the torsion angle per unit length τ(z). Similarly, on the proximal side of the capture node 64, it may be joined to the region of weakest torsional rigidity 68 by a suitable smooth curve 96.

The cutting edges 94 may vary in detailed shape to allow files that cut smoothly, or aggressively or have more of a rasping action. Such cutting edge variations are well known in the art. Each type of cutting edges 94 may be useful at various stages of removing the dental pulp 20 from the canals 22.

The shaft to handle transition 98 should also be by means of a smooth curve 96 that avoids any discontinuities in the torsion angle per unit length τ(z) as such discontinuities may result in concentration of torque forces and lead to deformation or breakage.

FIG. 5c shows a close-up schematic view of the working portion 66 of the quasi-hyperbolic endodontic instrument 92, showing the cutting edges 94 and the pilot tip 100.

FIG. 5d shows a close-up schematic view of the proximal end of the quasi-hyperbolic endodontic instrument 92. The view shows the smooth curve 96 that connects the capture node 64 to the flexible shaft 70, as well as the smooth curve 96 that connects the capture node 64 to the region of weakest torsional rigidity 68. The view also shows the shaft to handle transition 98 that is a smooth curve connecting the region of weakest torsional rigidity 68 to the handle 72.

FIG. 5e shows a cross-sectional view drawn on "AA" showing the cutting edges 94 formed by four grooves ground into the working portion 66 of the flexible shaft 70.

FIG. 5f shows a cross-sectional view drawn on "BB" showing flat facets 102 and an hexagonal cross section. The flat facets 102 that may facilitate both clamping during calibration of the quasi-hyperbolic endodontic instrument 92, and the removal of the broken quasi-hyperbolic endodontic instrument 92.

FIG. 6a shows a schematic, sectional side view of a cable endodontic instrument 104 of the present invention. In a preferred embodiment, the cable endodontic instrument 104 may have a cable 106. The proximal end 78 of the cable 106 may be enclosed by a cylindrical tube 108. The cylindrical tube 108 in turn may fit into a handle 72 that is attached to a drill attachment mechanism 74. The handle 72 may have a slideably attached depth indicator 80. At the distal end 76 of the cable 106 a working portion 66 may be attached to the cable 106.

FIG. 6b shows a view of an exemplary flexible endodontic file 110 of the present invention.

The cable 106 may be made from a number of strands of metal wire 112. The strands of metal wire 112 may be made from suitable metal or metal alloys such as, but not limited to, stainless steel, TiNi alloy or a super-elastic Nickel, Titanium and Niobium alloy or some combination thereof. The strands of metal wire 112 may be substantially equal in length and may be helically wound around a central strand. The cable 106 is substantially uniform in cross-section and therefore has a substantially uniform torsion angle per unit length τ(z).

The proximal end 78 of the cable 106 may be encased in a cylindrical metal tube made from a suitable metal or metal alloys such as, but not limited to, stainless steel, TiNi alloy, silver, gold, titanium or a super-elastic Nickel, Titanium and Niobium alloy or some combination thereof. The cable 106 may be fixed to the cylindrical tube 108 by, for instance, welding. The cylindrical tube 108 allows the flexible endodontic file 110 to have the required stiffness for cutting and the necessary overall length.

The distal end 76 of the cable 106 may be attached to the cutting head 67 of the flexible endodontic file 110. The cutting head 67 may include one or more cutting blades 114 and a pilot tip 100. The pilot tip 100 may be shaped as a portion of a sphere, such as, but not limited to, a hemisphere. The pilot tip 100 preferably has a diameter that is about 50% of the diameter of the cable 106, though it may vary from 20% to 80% of the diameter. The cutting blades 114 may be made from a suitable metal or metal alloys such as, but not limited to, stainless steel, TiNi alloy, silver, gold, titanium or a super-elastic Nickel, Titanium and Niobium alloy or some combination thereof, and may be attached to the cable 106 by, for instance, welding or brazing. Stainless steels typically contain elements selected from a group such as, but not limited to, Chrome, Nickel, Molybdenum and Titanium or a combination thereof. The amount of such elements may vary from as little as 1% to as much as 20%. Chrome may, for instance, be incorporated in a steel alloy at a percentage of weight ranging from 10% to 15%.

The cutting head 67 with the cutting blades 114 may, for instance, be turned from a stainless steal tube that may be soldered on to the distal end of the cable 106. In an alternate embodiment, the cutting head 67 may be made form the cable 106 by, for instance welding and grinding.

FIG. 6c shows the cable 106 attached to the working portion 66 of the flexible endodontic file 110 showing the strands of metal wire 112 of the cable, the cutting blades 114 and the pilot tip 100.

FIG. 6d shows a cross section on "CC", showing the cutting blades 114.

FIG. 6e shows a cross-section on "DD", showing the cylindrical tube 108 and the strands of metal wire 112.

FIG. 6f shows a cross-section view of a cable 106 have seven strands of metal wire 112. The six outer strands of metal wire 112 are helically wound around the central strand of metal wire 112.

FIG. 6g shows a cross-section view of a cable 106 have nineteen strands of metal wire 112.

The cable endodontic instruments 104 are preferably made to satisfy ISO standards and be manufactured having cutting diameters such as, but not limited to, diameters of 0.08 mm, 0.1 mm, 0.15 mm, 0.2 mm and 0.25 mm.

TABLE 1

| No | Thickness of wire | Thickness of cable | Kind of tubing | Strain in fiber | Comments |
| --- | --- | --- | --- | --- | --- |
| 1 | 16 µm | $_{1\times19}$= 80 µm | 32 REG, ACCU-TUBE | 0.4% | R = 2 mm |
| 2 | 20 µm | $_{1\times19}$= 100 µm | 17-7, ACCU-TUBE | 0.5% | R = 2 mm |
| 3 | 30 µm | $_{1\times19}$= 150 µm | 29 REG, ACCU-TUBE | 0.75% | R = 2 mm |
| 4 | 38 µm | $_{1\times19}$= 190 µm | 27 REG, ACCU-TUBE | 0.95% | R = 2 mm, $_{head}$= 200 µm |
| 5 | 46 µm | $_{1\times19}$= 230 µm | 26 REG, ACCU-TUBE | 1.15% | R = 2 mm, $_{head}$= 250 µm |
| 6 | 66 µm | $_{1\times19}$= 330 µm | 24 TW, ACCU-TUBE | 0.85% | R = 4 mm, $_{head}$= 350 µm |

Table 1 shows the calculated strain in cable fibers for cables corresponding to the ISO standard sizes detailed above. The calculations are shown in detail in, for instance, U.S. Provisional Patent Application No. 61/231,474 filed on Aug. 5, 2009 by E. Rzhanov et al. titled "High Safety Files for Root Canal Treatment", the contents of which are hereby incorporated by reference, or some combination thereof. The depend on the derived relationship:

$$\sigma_{zzmax} = E \cdot \frac{r}{R}$$

in which r represents the radius of the strands of metal wire 112, R represents the radius curvature of the canals 22 that the instrument is working on E represents Young's modulus of elasticity for the material that the strands of metal wire 112 are made of, and $\sigma_{zz\,max}$ represents the maximum stress in the strands of metal wire 112. In Table 1, R is either 2 mm or 4 mm.

Permissible stress for stainless steel has experimentally been found to be 1.5 to 2.0%. This is the strain at which stainless steel will begin to deform non-elastically.

As can be seen from Table 1, for a seventeen strand cable, the maximum strain in each strand for all the ISO radius instruments, is well below the maximum permissible strain for the practical flexibility needed in performing endodontic procedures on teeth.

Although the invention has been described in language specific to structural features and/or methodological acts, it is to be understood that the invention defined in the appended claims is not necessarily limited to the specific features or acts described. Rather, the specific features and acts are disclosed as exemplary forms of implementing the claimed invention. Modifications may readily be devised by those ordinarily skilled in the art without departing from the spirit or scope of the present invention.

The invention claimed is:

1. A cable endodontic file, comprising:
a cable comprising at least seven substantially identical strands of metal wire each having substantially equal diameter and substantially equal lengths, and having six of said strands helically wound around the seventh strand, thereby forming said cable having a proximal end, a distal end and an axis of rotation extending from said distal end to said proximal end;
a cutting head fixedly attached to the distal end of said cable, said cutting head having at least one flat cutting surface oriented in a plane containing said axis of rotation;
a handle comprising a metal tube enclosing part of said cable and being fixedly attached to the proximal end to said cable, and wherein the unenclosed portion of the cable extends at least one third of the length of the combined cable and the enclosing metal tube, and
a pilot tip located proximate to the distal end of said cutting head, said pilot tip being a spherical cap having a base diameter substantially equal to the diameter of said cable.

2. The file of claim 1 wherein said fixed cutting head comprises a metal tube, attached to the distal end of said cable, and being formed to provide one or more cutting edges.

3. The file of claim 1 wherein said metal is an alloy comprising stainless steel or at least 1% by weight of one of Chrome, Nickel, Molybdenum and Titanium or a combination thereof.

* * * * *